(12) United States Patent
Macrae et al.

(10) Patent No.: US 7,465,848 B2
(45) Date of Patent: Dec. 16, 2008

(54) ZEBRAFISH ASSAY

(75) Inventors: Calum A. Macrae, Newton Center, MA (US); David J. Milan, Boston, MA (US); C. Geoffrey Burns, Boston, MA (US); Randall Peterson, Stoneham, MA (US); Travis Peterson, Naperville, IL (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/149,662

(22) Filed: Jun. 10, 2005

(65) Prior Publication Data

US 2006/0015948 A1  Jan. 19, 2006

Related U.S. Application Data

(63) Continuation-in-part of application No. 10/605,415, filed on Sep. 29, 2003, now abandoned.

(60) Provisional application No. 60/427,753, filed on Nov. 20, 2002.

(51) Int. Cl.
*A61K 49/00* (2006.01)
*G01N 33/00* (2006.01)
*A01K 67/00* (2006.01)
*A01K 67/033* (2006.01)
*A01K 67/027* (2006.01)

(52) U.S. Cl. .............................. 800/13; 800/3; 800/20; 424/9.2

(58) Field of Classification Search .................... 800/3, 800/20; 514/9.2
See application file for complete search history.

(56) References Cited

U.S. PATENT DOCUMENTS

| | | | |
|---|---|---|---|
| 4,603,209 A | 7/1986 | Tsien et al. | |
| 5,049,673 A | 9/1991 | Tsien et al. | |
| 6,299,858 B1 | 10/2001 | Serbedzija et al. | |
| 6,380,458 B1 | 4/2002 | Lin | |
| 6,656,449 B1 * | 12/2003 | Serbedzija et al. | 424/9.2 |
| 2002/0165364 A1 | 11/2002 | Tsien et al. | |
| 2003/0074682 A1 | 4/2003 | Langheinrich | |
| 2003/0161787 A1 | 8/2003 | Langheinrich | |
| 2003/0162292 A1 | 8/2003 | Tsai et al. | |
| 2004/0133144 A1 | 7/2004 | Macrae et al. | |
| 2005/0155087 A1 * | 7/2005 | Zon et al. | 800/3 |

FOREIGN PATENT DOCUMENTS

| | | | |
|---|---|---|---|
| WO | WO01/92874 | * | 12/2001 |
| WO | WO2004/047634 | | 6/2004 |

OTHER PUBLICATIONS

Kuhl, M. Frontiers in Bioscience, 9:967-974, 2001.*
Peterson RT. et al. ,PNAS, 97:12965-12969, 2000.*
Barrionuevo & Burggren "0$_2$ consumption and heart rate in developing zebrafish (*Danio rerio*): influence of temperature and ambient 0$_2$" *American Physiological Society*, vol. 276(2): R505-R513 (1999).
Camm et al. "Congenital and acquired long QT syndrome" *European Heart Journal*, vol. 21: 1232-1237 (2000).
Chen et al. "Mutations affecting the cardiovascular system and other internal organs in zebrafish" *Development*, vol. 123: 293-302 (1996).
Culp et al. "High-frequency germ-line transmission of plasmid DNA sequences injected into fertilized zebrafish eggs" *Proc. Natl. Acad. Sci.*, vol. 88: 7953-7957 (1991).
Huang et al. "Germ-Line transmission of a myocardium-specific GFP transgene reveals critical regulatory elements in the cardiac myosin light chain 2 promoter of zebrafish" *Developmental Dynamics*, vol. 228: 30-40 (2003).
Keating & Sanguinetti "Molecular and cellular mechanisms of cardiac arrhythmias" *Cell*, vol. 101(4): 569-580 (2001).
Rottbauer et al. "Growth and function of the embryonic heart depend upon the cardiac-specific 1-type calcium channel α1 subunit" *Developmental Cell*, vol. 1: 265-275 (2001).
Sehnert & Stainier "A window to the heart: can zebrafish mutants help us understand heart disease in humans?" *Trends in Genetics*, vol. 18(10): 491-494 (2002).
Stuart et al. "Replication, integration and stable germ-line transmission of foreign sequences injected into early zebrafish embryos" *Development*, vol. 103(2): 403-412 (1988).
Stuart et al. "Stable lines of transgenic zebrafish exhibit reproducible patterns of transgene expression" *Development*, vol. 109: 577-584 (1990).
Thisse & Zon "Organogenesis—heart and blood formation form the zebrafish point of view" *Science*, vol. 295: 457-462 (2002).
Warren et al. "The genetic basis of cardiac function: dissection by zebrafish (*Danio rerio*) screens" *Phil. Trans. R. Soc. Lond.*, vol. 355: 939-944 (2000).
Warren et al. "The slow mo mutation reduces pacemaker current and heart rate in adult zebrafish" *Am J Physiol Heart Circ Physiol*, vol. 281: H1711-H1719 (2001).
Miller et al., "Imaging [$Ca^{2+}$] with aequorin using a photon imaging detector," Methods Cell Biol. 40:305-38 (1994).

(Continued)

*Primary Examiner*—Valarie Bertoglio
(74) *Attorney, Agent, or Firm*—Fish & Richardson P.C.

(57) ABSTRACT

The invention includes a zebrafish assay for cardiac response.

27 Claims, 3 Drawing Sheets

OTHER PUBLICATIONS

Molecular Probes, "AquaLite® Recombinant Aequorin (A-6785)," MP 06785 (2001).

Office Action dated Apr. 25, 2007 in U.S. Appl. No. 10/605,415.

Bridge et al., "The relationship between charge movements associated with $I_{Ca}$ and $I_{Na\text{-}Ca}$ in cardiac myocytes," Science, 24:376-378, (1990).

Ebert et al., "Calcium extrusion is critical for cardiac morphogenesis and rhythm in embryonic zebrafish hearts," Proc. Natl. Acad. Sci. USA, 102:17705-10 (2005).

Garrity et al., "The *heartstrings* mutation in zebrafish causes heart/fin Tbx5 deficiency syndrome," Development, 129:4635-45, (2002).

Lagenbacher et al., "Mutation in sodium-calcium exchanger 1 (NCX1) causes cardiac fibrillation in zebrafish," Proc. Natl. Acad. Sci. USA, 102:17699-17704 (2005).

Wakimoto et al., "Targeted disruption of $Na^+/Ca^{2+}$ exchanger gene leads to cardiomyocyte apoptosis and defects in heartbeat," J. Biol. Chem., 275:36991-98 (2000).

Griffith, NCBI Accession No. BX248505, (2005).

PCT Written Opinion of PCT/US06/22295.

International Search Report of PCT/US06/22295.

* cited by examiner

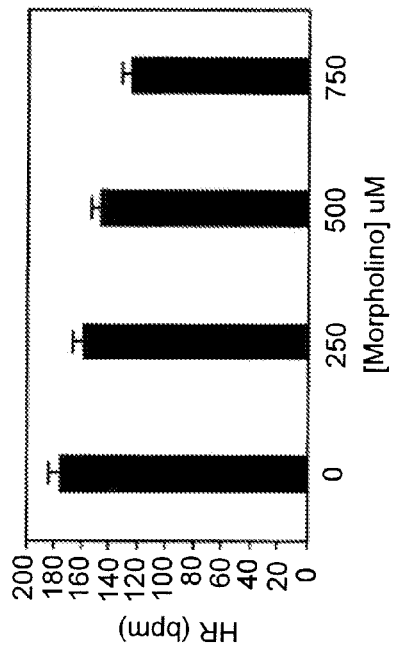
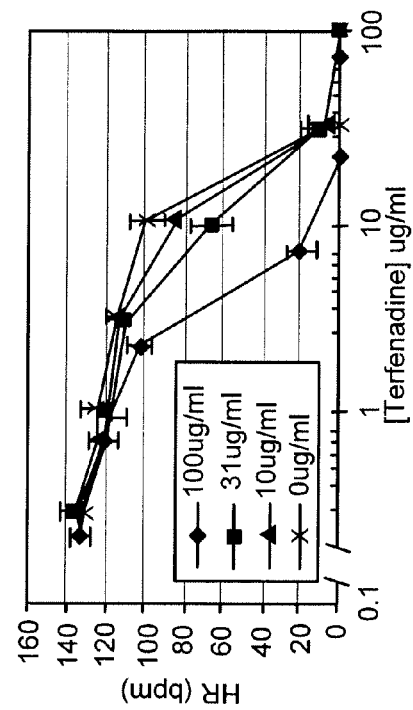
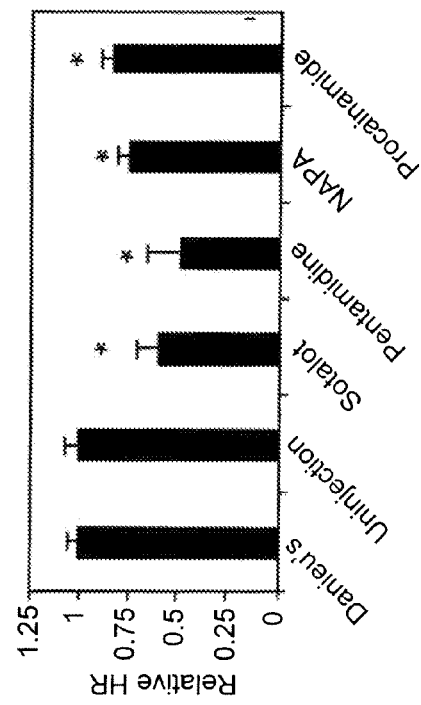
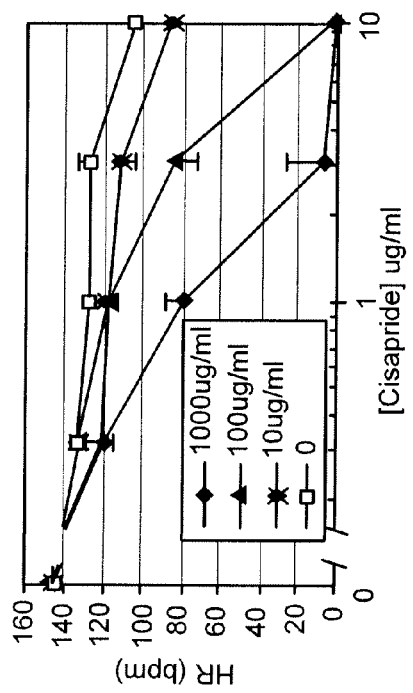

ZEBRAFISH ASSAY

CROSS-REFERENCE TO RELATED APPLICATIONS

This application is a continuation-in-part of U.S. Ser. No. 10/605,415, filed Sep. 29, 2003, now abandoned, which claims the benefit of U.S. Provisional Application 60/427,753, filed Nov. 20, 2002, the contents of each of which are incorporated herein by reference.

GOVERNMENT RIGHTS

This invention was made with United States Government support under award number 1K08HL068711-01 awarded by the National Institutes of Health. The United States Government has certain rights in the invention.

BACKGROUND

Side effects, e.g., cardiovascular (CV)-related side effects, of pharmaceutical agents can cause significant and often unpredictable clinical problems. For example, prolongation of the QT interval is an undesired and often unanticipated side effect of many cardiac and non-cardiac drugs, as it predisposes the patient to the potentially fatal arrhythmia Torsades de Pointes (TdP). Several pharmaceutical agents have been withdrawn from the U.S. market due to TdP. Many medications only cause QT prolongation when administered in combination with other drugs. QT prolongation can occurs as a result of inherited mutations in ion channel genes, or more commonly as a consequence of drugs that affect cardiac repolarization [1, 2].

Model systems for either IKr blockade or QT prolongation include in vitro assays using cells which have been engineered to express KCNH2 and patch-clamping to directly measure the IKr current in the presence and absence of the drug in question. Voltage sensitive dyes have also been employed in such cells to detect changes in the time course of depolarization and repolarization. Whole animal systems such as guinea pigs, rabbits, or dogs are also used to evaluate drug induced cardiotoxicity.

SUMMARY

The invention is based, in part, on the discovery that the zebrafish larva provides an effective in vivo model system to screen for physiological effects, e.g., side effects, of pharmaceutical agents on an organ system, e.g., the cardiovascular system, renal system, neurobehavioral system, or other assayable system of the zebrafish. For example, we have found that the cardiovascular, e.g., cardiotoxic, effect of an agent, e.g., a drug, e.g., a small molecule drug, on the developing zebrafish cardiovascular (CV) system can predict the effects of the agent on the CV system in humans. We have developed a simple, high throughput, in vivo whole animal assay to evaluate compounds for their effect on cardiovascular function, e.g., heart rate. The assay can be used to evaluate, e.g., toxicity of a compound, drug interaction between a plurality of compounds, effects of metabolites of a compound, and/or absorption parameters of a compound, e.g., as they relate to CV function.

Accordingly, in one aspect the invention features a method of evaluating an agent, e.g., evaluating (e.g., predicting) an effect of a test agent, e.g., a small molecule, on a parameter of heart function (such as a parameter of heart contractility) in a subject, e.g., a human. The method includes: contacting a teleost (e.g., a zebrafish), preferably a larva, with a test agent; and evaluating a parameter of heart function, e.g., heart rate; ejection fraction, repolarization, calcium flux or concentration, or conduction velocity, or a calcium-based parameter of heart function (e.g., time to completion for a calcium transient or transient amplitude) in the teleost, e.g., the zebrafish. Preferably, the parameter of heart function is compared to a reference value, e.g., a baseline value or a control. The method can include correlating the effect of the agent on the teleost (e.g., zebrafish) with a predicted effect of the agent on a mammal, e.g., a human, e.g., by providing, (e.g., to the government, a health care provider, insurance company or patient) informational, marketing or instructional material, e.g., print material or computer readable material (e.g., a label), related to the agent or its use, identifying the effect of the agent as a possible or predicted effect of the agent in a mammal, e.g., a human.

The method can include identifying the agent as a cardiotoxic agent, e.g., in humans, if it causes a change in the parameter compared to a reference. For example, an agent can be identified if it has an effect (e.g., on a parameter described herein) that differs relative to a reference, e.g., to a statistically significant degree or to a degree recognizable to one in skilled the art. The reference can be a negative (or in some cases a positive control). In one embodiment, the agent is identified if it has an effect similar to a positive control (e.g., terfanadine or dofetilide). For example, the agent has an effect that is more similar to the positive than to another reference (e.g., a negative control, e.g., a negative control such as buffer alone). The identification can be in the form of informational, marketing or instructional material, e.g., as described hereinabove. In one embodiment, the method includes correlating a value for the evaluated parameter with cardiotoxicity or probability of cardiotoxicity, e.g., generating a dataset correlating a value for the evaluated parameter with cardiotoxicity or probability of cardiotoxicity.

The zebrafish is preferably a developing zebrafish, e.g., a pre-innervation larva.

The zebrafish, e.g., the zebrafish larva, can include a calcium responsive molecule, e.g., for detecting changes in intracellular calcium in at least one heart cell of the animal, e.g., in all heart cells of the animal. The calcium responsive molecule can be, for example, a dye such as calcium green, fura-2, indo-1, or fluo-3. The dye can be physically associated with another moiety, e.g., dextran. The calcium responsive molecule can be a protein, e.g., aequorin.

In a preferred embodiment, the method (as well as other related methods described herein) can be performed in parallel, e.g., using an array. For example, a plurality of zebrafish in an array are contacted, e.g., with different agents, different concentrations of the same agent, or the same agent in combination with different second agents. Each position (such as a well or unpartitioned region) on an array can include one or more zebrafish (e.g., three zebrafish larvae).

In a preferred embodiment, the parameter of heart function is heart rate (HR). A change, e.g., an increase or decrease in HR can be evaluated, e.g., by observing the zebrafish heart rate, e.g., by conventional light microscopy. A quantitative or qualitative change in HR can be evaluated. In one embodiment, the zebrafish heartbeat is recorded (e.g., optically, e.g., by video microscopy) and the evaluation of the effect of the agent on HR performed by analyzing the recording. In one embodiment, the heart rate can be visually detected and measured from the recording by one of ordinary skill in the art. In another embodiment, HR is obtained by measuring the average pixel intensity or density throughout a specified region of the heart, e.g., the atrium or ventricle, for a given time interval, and measuring the time between peaks. In a preferred embodiment, the evaluation is automated for high throughput, e.g., by processing of recordings with any imaging software known in the art, e.g., METAMORPH® software or any other appropriate software or method. Heart rate can also be used to normalize other parameters, e.g., or a calcium-based parameter (e.g., time to completion for a calcium transient such as CAT90).

In another embodiment, heart rate can be evaluated by detecting, e.g., measuring the QT interval, e.g., using a dye, e.g., a voltage sensitive dye or a calcium responsive dye. The parameters of heart function, e.g., heart rate, ejection fraction, repolarization, or conduction velocity, or a calcium-based parameter of heart function (e.g., time to completion for a calcium transient or transient amplitude) can also be evaluated by other techniques known to one of ordinary skill in the art. For example, ejection fraction and conduction velocity can be evaluated, e.g., by processing of recordings with any imaging software known in the art, e.g. METAMORPH®; repolarization can be evaluated, e.g., measured, by electrocardiographic recording.

The parameter of heart function can also be evaluated by performing an EKG on the zebrafish and detecting changes in the P wave, PR interval, PR segment, QRS complex, ST Segment, QT interval and/or T wave of the EKG. Rottbauer et al. (2001) Developmental Cell, Vol 1, 265-275, describe a method for recording an EKG in the zebrafish. A parameter of heart function, e.g., blood flow, can also be detected by injection of a detectable substance, e.g., a fluorescent compound, e.g., fluorescent beads, into the circulation, to allow direct visualization of the zebrafish circulation. Another technique can include soaking the embryo in a contrast agent, e.g., a BODIPY-ceramide contrast agent, and then estimating ejection fraction by measuring the area of the ventricle in diastole vs. systole. Circulation can also be visualized using a transgenic zebrafish line that expresses GFP (or other fluorescent protein) in red blood cells.

In one embodiment, the zebrafish is a transgenic zebrafish that expresses a detectable marker at least in a cell of the heart. For example, the zebrafish contains a transgene that includes a nucleic acid sequence encoding a detectable marker under control of a tissue specific, e.g., heart specific, regulatory region. In one embodiment, the detectable marker is a calcium-responsive protein, e.g., a protein whose properties change as a function of calcium concentration. For example, the detectable marker protein can be aequorin. In one embodiment, the detectable marker is a fluorescent protein, e.g., green fluorescent protein (GFP), enhanced GFP (EGFP), DsRed, or other naturally occurring or modified chromophore. In a preferred embodiment, the heart-specific regulatory region is a heart specific promoter or enhancer, e.g., a cardiac myosin promoter, e.g., a cardiac myosin heavy chain (cmhc) or light chain (cmlc) promoter. In a preferred embodiment, the promoter is a cmlc promoter or functional fragment thereof, e.g., a promoter described herein, e.g., a sequence that includes SEQ ID NO:1.

In another embodiment, the zebrafish has a tissue or organ that is tagged, e.g., fluorescent, thereby allowing more sensitive visualization of the tissue or organ. For example, the zebrafish comprises a heart-specific regulatory region (e.g., a heart-specific regulatory region described herein) operably linked to a nucleotide sequence encoding a fluorescent polypeptide, such as GFP, EGFP, or other naturally occurring or modified chromophore that can be used as a fluorescent marker. In such embodiments, the method can include steps for processing images of the fluorescent tissue (such as a series of images of fluorescent zebrafish tissues or organs). Such steps can include: scanning an array to identify each of a plurality of fluorescent regions (corresponding to regions of fluorescent hearts) whose maximum intensity is above a control value; optionally recording (e.g., by video recording) each of the identified regions for a specified time; calculating the average intensity through time for each of the plurality of fluorescent regions; and generating a dataset of the average intensity through time (periodicity) for each of the plurality of fluorescent regions. The processing steps can be implemented on a computer readable medium comprising a program which causes a processor to perform the steps of the processing method, or on an apparatus comprising a computer readable medium storing a program that causes a processor to perform the steps of the processing method. In one embodiment, a system to implement the method includes: an input port that receives the series of images; a data storage device, operably coupled with the input port, that stores the images; and a processor, operably coupled with the input port and data storage device, that registers the images, where the processor performs the processing steps.

In some embodiments, the zebrafish is contacted with a substance (e.g., a dye, e.g., a voltage sensitive dye) that allows more sensitive visualization of the CV system, e.g., the heart rate, e.g. the action potential duration. The dye can be a calcium responsive dye.

In some embodiments, a parameter of heart function, e.g., blood flow, can also be detected by injection of a detectable substance, e.g., a fluorescent compound, e.g., fluorescent beads, into the circulation, to allow direct visualization of the zebrafish circulation.

In some embodiments, a parameter of heart function, e.g. contraction fraction, can also be determined by measuring the areas of the ventricle during diastole and systole and estimating the output of the heart during each cardiac cycle according to the following formula:

$$\frac{\text{Ventricular } Area_{Diastole} - \text{Ventricular } Area_{Systole}}{\text{Ventricular } Area_{Diastole}}$$

In some embodiments, a parameter of heart function, e.g. ejection fraction, can also be determined by measuring the areas of the ventricle during diastole and systole and using these measurements to estimate the volumes of the ventricle during diastole and systole. The volume estimates are used to estimate the ejection fraction according to the following formula.

$$\frac{\text{Ventricular } Volume_{Diastole} - \text{Ventricular } Volume_{systole}}{\text{Ventricular } Volume_{Diastole}}$$

In some embodiments, one can circumvent the absorption barrier and increase the sensitivity of the assay by performing the assay on isolated zebrafish hearts or cardiomyocytes, (e.g., using a technique for isolating zebrafish hearts or cardiomyocytes described herein). In other embodiments, one can circumvent the absorption barrier and increase the sensitivity of the assay by permeabilizing the fish, e.g., using a technique described herein.

In some embodiments, the method includes a second evaluation. In one embodiment, the evaluation of the same parameter of heart function can be repeated at least once with the same agent. In another embodiment, a different parameter of heart function is evaluated in the first and second evaluation steps. For example, heart rate is evaluated in the first evaluation step, and ejection fraction is evaluated in the second evaluation step. Similarly, a third or fourth evaluation step can be performed. In some embodiments, the second (or subsequent) evaluation(s) can include evaluating the effect of the same agent at a different concentration or the effect of the agent in combination with a second agent.

In some embodiments, the effect of a first test agent is evaluated in combination with at least a second test agent. In one embodiment, the first and second test agents are contacted simultaneously with the zebrafish. In another embodiment, the first and second agents are contacted consecutively, and the evaluation of the subject parameter, e.g., HR, performed before, after, and/or between contacting of the first and second agent. In one embodiment, the first agent may be removed before the second agent is contacted.

In some embodiment, a plurality of parameters are assessed. The plurality of parameters can be stored, e.g., in a database, e.g., as a profile of a test agent or of a genetic alteration (e.g., in a particular animal). The plurality of parameters can include, for example, two or more of any parameters described herein, e.g., heart rate, AV block, a calcium-based parameter, and voltage and calcium mapping.

The test agent can be any compound that is used or is being considered for use as a pharmaceutical agent, including a small molecule, DNA molecule, RNA molecule or polypeptide. In a preferred embodiment, the agent is a small molecule, e.g., a small chemical molecule. The test agent can be an antihistamine, antibiotic, antipsychotic, antiarrhythmic, microtubule inhibitor, hormone, anticonvulsant, antidepressant, analgesic, angiogenesis inhibitor, antiepileptic, neurostimulant, or chemical with an unknown physiological target or function.

In one embodiment, the test agent is added to the culture medium of the zebrafish. In other embodiments, the test agent (e.g., a hydrophilic molecule or a large molecule, e.g., a protein or DNA or RNA molecule) is injected into the zebrafish, e.g., into the yolk sac, into any embryonic cell or cells, or into the pericardium.

In one embodiments, the zebrafish has a genetic alteration in one or more genes related to heart function, e.g., in an ion channel component gene; a calcium channel or potassium channel gene. Such genes are described, e.g., in Warren et al., 2000, Philos Trans R Soc Lond B Biol Sci. 355(1399):939-44; and Chen et al., Development, 1996, 123:293-302. For example, the zebrafish can have a genetic alteration in the KCNH2, KCNE2 or cytochrome P gene. The genetically altered zebrafish can be genetically engineered or can be a naturally occurring or chemically induced mutant. The genetically altered zebrafish can have a more sensitive drug response or a less sensitive drug response and can increase specificity of the response.

In one embodiment, a transgenic zebrafish expresses a wild-type or mutant protein(s) in the embryonic heart. In one embodiment, a transgenic zebrafish expresses a protein in the embryonic heart under control of a cardiac-specific promoter, e.g. the cmlc promoter described herein, that increases or decreases the sensitivity of the heart to agents that prolong the QT interval in humans. For example, the transgenic zebrafish may overexpresses KCNH2 and/or KCNE2 proteins.

In some embodiments, the culture media of the zebrafish is standard media, e.g., E3 media. In one embodiment, the media is potassium depleted.

In one embodiment, the method includes the step of administering the agent to a second zebrafish. In another embodiment, the method includes administering the agent to a non-zebrafish animal, e.g., a mammal, e.g., an experimental rodent or primate.

In one embodiment, the agent is metabolized by the zebrafish, e.g., by the kidney, gastrointestinal tract, or liver of the zebrafish.

The zebrafish assays described herein are adaptable to read out any biological activity that might manifest as a change in heart rate. For example, the assay could be readily adapted to screen for drugs that have specific effects on the activity of any of the cytochrome p450s, e.g., cytochrome p450s which interact with cardioactive drugs or cytochrome p450 inhibitors.

The method can also be used to predict clinical implications of pharmaceutical agents by assaying changes in any other system of the zebrafish, e.g., zebrafish larva, that is readily detectable or assayable in the whole animal (e.g., by optical visualization), e.g., the kidney, liver, GI tract, or neurobehavioral system. The method can be used with other teleosts, e.g., other teleost larvae.

Each of these embodiments is equally applicable to other aspects and methods described herein.

In another aspect, the invention features a method of evaluating an agent, e.g., determining if a test agent is cardiotoxic. The method includes: contacting a zebrafish, preferably a developing zebrafish, with a test agent; and determining if the test agent causes an arrhythmia (e.g., bradycardia or tachycardia) in the zebrafish, wherein the test agent is identified as a cardiotoxic agent if it causes arrhythmia. The cardiotoxicity (or lack thereof) of the agent in the zebrafish is correlated with possible or predicted cardiotoxicity in humans.

In one embodiment, the determining step includes measuring the heart rate of the zebrafish as compared to a reference or control value, e.g., a known baseline value, the heart rate of the zebrafish before treatment, or a different untreated zebrafish. Bradycardia, as used herein, is a measurable decrease in heart rate. Tachycardia, as used herein, is a measurable increase in heart rate. The method can also include evaluating a calcium-based parameter, e.g., as described herein.

In one embodiment, the method includes generating a dataset correlating the determination of arrhythmia with cardiotoxicity or a probability of cardiotoxicity of the agent.

In another embodiment, the determining step includes evaluating the QT interval in the zebrafish. Preferably, the QT interval is compared to a reference value, e.g., a baseline value or a QT interval of a control zebrafish. An agent that decreases or decreases the QT interval by a measurable amount is identified as a cardiotoxic agent. For example, an agent that increases or decreases the QT interval by at least 1%, preferably at least 2%, more preferably at least 5%, 10%, 15%, 20% or more, is identified as a cardiotoxic agent.

In another aspect, the invention features a method of evaluating the effect of a plurality of compounds on a parameter of heart function, e.g., a calcium-based parameter of heart function. The method includes contacting a zebrafish with a plurality of compounds, and evaluating a parameter of heart function in the zebrafish, e.g., heart rate; ejection fraction, repolarization, or conduction velocity or a calcium-based parameter of heart function (e.g., time to completion for a calcium transient or transient amplitude. Preferably, the parameter is compared to a reference value, e.g., a baseline value or a control (e.g., a positive or negative control). In one embodiment, the method includes generating a dataset correlating each of the plurality of compounds with a value corresponding to the parameter evaluated, and optionally correlating each value with cardiotoxicity (or a probability of cardiotoxicity) or lack thereof.

The plurality of compounds can be contacted with the zebrafish simultaneously or separately. In one embodiment, a first compound of the plurality is contacted, an evaluation is performed, a second compound of the plurality is contacted, and a second evaluation is performed. In another embodiment, the plurality of compounds is contacted with the zebrafish together, e.g., simultaneously or nearly simultaneously, before an evaluation is performed. In one embodiment, a first compound of the plurality is removed before a second compound of the plurality is contacted. The time between the contacting of the first and second compounds of the plurality can, e.g., 15, 30, 45 seconds, or more, e.g., 1, 2, 3, 4, 5 or 10, 30 minutes, an hour or more.

In one embodiment, one of the plurality of compounds is a hormone, e.g., progesterone.

In another aspect, the invention features a method of evaluating the effect of a plurality of different treatments, e.g., a plurality of different compounds; a compound at a plurality of different concentrations or dosages; a compound in combination with a plurality of different second agents. The method includes: (a) providing an array of a plurality of individual regions, wells or addresses, each region, well or address of the plurality comprising a zebrafish (e.g., a zebrafish larva) being provided with a test treatment that differs from those at other regions, wells or addresses of the plurality; and (b) evaluating a parameter related to heart function of the zebrafish at each of the plurality of regions, wells or addresses. The method can include the use of microscopy, e.g., light microscopy, e.g., video light microscopy, to detect and record the effect of the different treatments on the zebrafish CV system. The method can also include an array member to contact the plurality of treatments with each of the plurality of regions, wells or addresses. Contacting the zebrafish with the treatments can be performed by, e.g., administering a compound to the culture media of the zebrafish; or injecting a compound into the zebrafish e.g., into the yolk sac, into any embryonic cell or cells, or into the pericardium. The parameter, e.g., heart rate, ejection fraction, repolarization, or conduction velocity can be evaluated by techniques known in the art, e.g., as described herein.

In a preferred embodiment, the array includes at least 4 addresses, more preferably 8, 16, 32, 64, 96, 128 or 384 addresses.

This method can be used to provide a high throughput assay for evaluating the cardiac effects of drugs or combinations of drugs. In one embodiment, the method includes generating a dataset providing any one or more of: a value for the evaluated parameter for each of the plurality of wells, regions or addresses; a value for the probability of cardiotoxicity for the treatment at each of the plurality of wells, regions or addresses.

In another aspect, the invention features a method of identifying a gene that affects a drug response. The method includes: (a) providing a test zebrafish having a genetic alteration in a gene (e.g., a genetically engineered or chemically mutated zebrafish); (b) contacting the test zebrafish with a drug, e.g., a small molecule drug; and (c) evaluating a parameter of heart function, e.g., heart rate, of the test zebrafish, wherein if the parameter (e.g., heart rate) of the test zebrafish, compared to a wildtype zebrafish, is increased or decreased, the gene is identified as a gene that affects a drug response.

In a preferred embodiment, the test zebrafish has decreased heart rate in response to the drug compared to a wildtype zebrafish, e.g., the test zebrafish is more sensitive to a QT prolonging drug than a wildtype zebrafish. Such zebrafish can be used in other assays described herein to increase the sensitivity of the assay.

In a preferred embodiment, the method further includes determining if the increase or decrease in drug response is heritable (e.g., by growing the positive test zebrafish) and positionally cloning the gene using standard techniques. Once a gene or genetic alteration that affects a drug response is so identified, a human homolog can be identified by conventional techniques. A patient can then be screened for the presence or absence of the subject gene or genetic alteration (e.g., polymorphism or mutation). This information can be used to determine whether the patient is susceptible to cardiotoxic side effects of a particular drug or combination of drugs.

In a preferred embodiment, the method further includes any one or more of: identifying the gene or genetic alteration, isolating the gene or the genetic alteration, cloning the gene or genetic alteration, sequencing the gene or genetic alteration, or detecting a difference in gene expression in the positive test zebrafish compared to wildtype.

In another aspect, the invention features a method of detecting a zebrafish mutant having a response to an agent or a phenotype characterized by a change in the morphology or movement of an organ or tissue, e.g., the heart, GI tract, liver or kidney. The method includes providing a test zebrafish larva; and examining the zebrafish larva with an optical recording device, optionally connected to a computer, to detect the change in morphology or movement. In a preferred embodiment, the change is a change in a periodic movement, e.g., heart rate. The method can include the use of an array of a plurality of test zebrafish, as described herein.

In one embodiment, the zebrafish is contacted with a compound (e.g., a detectable substance, e.g., a fluorescent compound, e.g., fluorescent beads, or a dye, e.g., a voltage sensitive dye) that allows more sensitive visualization of zebrafish organs.

In one embodiment, the zebrafish comprises a fluorescent tissue or organ, e.g., as described herein, thereby allowing more sensitive visualization of the tissue or organ. For example, the zebrafish comprises a heart-specific regulatory region operably linked to a nucleotide sequence encoding a fluorescent polypeptide, such as GFP, EGFP, or other naturally occurring or modified chromophore that can be used as a fluorescent marker.

In another aspect, the invention features a method for processing a series of fluorescent images in an array (such as a series of images of fluorescent biological tissues, organs or organisms, e.g., zebrafish or zebrafish organs or tissues). The method includes: scanning the array to identify each of a plurality of fluorescent regions whose maximum intensity is above a control value; optionally recording (e.g., by video recording) each of the identified regions for a specified time; calculating the average intensity through time for each of the plurality of fluorescent regions; and generating a dataset of the average intensity through time (periodicity) for each of the plurality of fluorescent regions. The invention also features a computer readable medium comprising a program which causes a processor to perform the steps of the processing method. Also featured is an apparatus comprising a computer readable medium storing a program that causes a processor to perform the steps of the processing method. The invention also features a system for processing a series of images. The system includes: an input port that receives the series of images; a data storage device, operably coupled with the input port, that stores the images; and a processor, operably coupled with the input port and data storage device, that registers the images, where the processor performs the steps of the processing method.

In another aspect, the invention features an isolated nucleotide sequence that includes SEQ ID NO:1 (and a vector and host cell that includes the isolated nucleotide sequence). SEQ ID NO:1 is a fragment of the regulatory region of the zebrafish cardiac myosin light chain (cmlc) gene. SEQ ID NO:1 is necessary and sufficient to drive cardiac specific expression in zebrafish, e.g., in embryonic cardiomyocytes. A nucleotide sequence comprising SEQ ID NO:1 can be operably linked to a heterologous protein, e.g., a marker protein, e.g., a fluorescent marker such as GFP, EGFP, DsRed or other chromophore, to drive expression of fluorescent proteins in the myocardial cell nucleus, cytoplasm, at the myocardial cell and/or at the plasma membrane. The heterologous protein can also be a calcium responsive protein, e.g., aequorin. It is understood that a nucleotide sequence having a limited number of additional nucleotides found in nature at the 5' and/or 3' end of SEQ ID NO:1 could also be used. For example, a promoter fragment that includes SEQ ID NO:1 and less than 10000, preferably less than 8000, 5000, 1000, 750, more preferably less than 500, 400, 300, 200, 150, 100, 75, 50, 30, or fewer, nucleotides normally found 5' and/or 3' of SEQ ID NO:1 can also be used.

In one embodiment, the nucleotide sequence, vector, host cell or zebrafish includes SEQ ID NO:1 operably linked to a nucleotide sequence encoding a heterologous polypeptide, e.g., a polypeptide not normally expressed in the heart, e.g., detectable marker, e.g., a fluorescent protein, e.g., GFP, EGFP, EBFP, EYFP, DsRed or modified variants thereof, aequorin or other calcium responsive protein.

In one embodiment, a construct is provided that includes: (a) a first expression cassette having a cardiac promoter, e.g., a cardiac promoter described herein, e.g., a cmlc promoter (e.g., SEQ ID NO:1) operably linked to a sequence encoding a detectable marker, e.g., a fluorescent marker protein described herein, e.g., GFP, EGFP, dsRed, dsRed2, or other chromophore, aequorin or other calcium responsive protein and (b) a second expression cassette having the same promoter as the first cassette, arranged such that a nucleotide sequence coding for any protein of interest can be cloned in an operably linked manner to the promoter of the second cassette. For example, the second cassette can include the same promoter as the first cassette, linked to a multi-cloning site (MCS) and a polyadenylation signal such that a protein of interest can be cloned into the multi-cloning site. The construct is useful for co-expressing a protein of interest along with a marker protein in a heart tissue.

In another aspect, the invention features a method of co-expressing a plurality of proteins in a zebrafish heart. The method includes injecting a zebrafish (e.g., an embryo) with a plasmid that contains at least two expression cassettes in a single DNA construct. Each expression cassette includes a regulatory region (e.g., a promoter) from the same or different cardiac-specific gene, e.g., a cardiac myosin subunit, such as cardiac myosin light chain or heavy chain (e.g., MLC2a, e.g., SEQ ID NO:1). In the first cassette, the promoter drives expression of a subject protein. In the second cassette, the promoter drives expression of a detectable marker. The detectable marker serves as a marker for the cardiomyocytes expressing the subject protein. The construct is useful for co-expressing a protein of interest along with a marker protein in the heart tissue.

In another aspect, the invention features a method of harvesting (e.g., isolating) zebrafish embryonic hearts and/or cardiomyocytes. The method includes (a) providing a zebrafish (e.g., a zebrafish larva) that carries a nucleotide sequence that includes SEQ ID NO:1 operably linked to a nucleotide sequence encoding a heterologous polypeptide, e.g., a detectable marker, e.g., a fluorescent protein, e.g., GFP, EGFP, EBFP, EYFP, DsRed or modified variants thereof, aequorin or other calcium responsive protein; (b) dissociating the zebrafish, e.g., the zebrafish embryos (e.g., with a mucolytic agent and protease such as collagenase or by mechanical dissociation); and (c) detecting, selecting, harvesting or isolating the intact heart via the detectable marker, e.g., by fluorescence. Alternatively, intact hearts can be digested to completion with a protease and individual cardiomyocytes that express the detectable marker are purified with fluorescence activated cell sorting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A-D are graphs showing the effect on zebrafish HR of: (2A) direct injection of each indicated drug; (2B) antisense morpholino oligonucleotides directed against zebrafish KCNH2; (2C) interaction of erythromycin and cisapride; and (2D) interaction of cimetidine and terfenadine (FIG. 2D).

DETAILED DESCRIPTION

The inventors have developed a simple, sensitive, high-throughput, in vivo assay that can predict the cardiac effects, e.g., effects on QT interval and heart rate, of pharmaceutical compounds, e.g., small molecule drugs, in mammals, e.g., humans. Exemplary parameters that can be evaluated include parameters associated with calcium transients or calcium flux, e.g., as described herein. Such information is particularly useful for discriminating between toxic effects of an agent relative to other mechanisms of bradycardia. As discussed in detail below, zebrafish bradycardia consistently and reproducibly predicted clinical repolarization abnormalities and faithfully recapitulated the effects of known drug-drug interactions on cardiac function for a broad collection of biologically active compounds, e.g., small molecules.

Zebrafish

Zebrafish have a full complement of vertebrate organs including a heart, gastrointestinal tract, liver and kidneys. It has been found that zebrafish can serve as a proxy for recapitulation and detection of drug-drug interactions, including drug metabolism or drug displacement, that take place at many levels in higher animals, such as mammals, e.g., humans. The presence of these organs also allows for the detection of effects due to active metabolites of the primary drugs.

The zebrafish has a beating heart with a complex repertoire of ion channels, and functioning metabolism within 24 hours of fertilization [7]. In addition, dramatic effects on HR and function are tolerated by the larval fish which survive for 4-5 days without a functioning circulation [8].

It has been found that *Danio rerio* (zebrafish) can serve as a model system to predict the cardiac effects in humans of a compound or combination of compounds. In particular, it has been found that zebrafish embryos have a marked sensitivity to drugs that prolong the QT interval, manifesting as a decrease in heart rate. The transparency of the embryo facilitated rapid evaluation of heart rate (HR) and rhythm.

Cardiac Function Assay

During a screen for the effects of 100 small molecules on cardiac function (e.g., heart rate) of the zebrafish, *Danio rerio*, drugs that cause QT prolongation in humans consistently caused bradycardia and AV block in the zebrafish. 22 of 23 compounds that cause repolarization abnormalities in humans caused similar effects in the cardiotoxicity assay described herein. In addition, classical drug-drug interactions between ketoconazole and terfenadine as well as erythromycin and cisapride were faithfully reproduced in this system.

Figure 1:
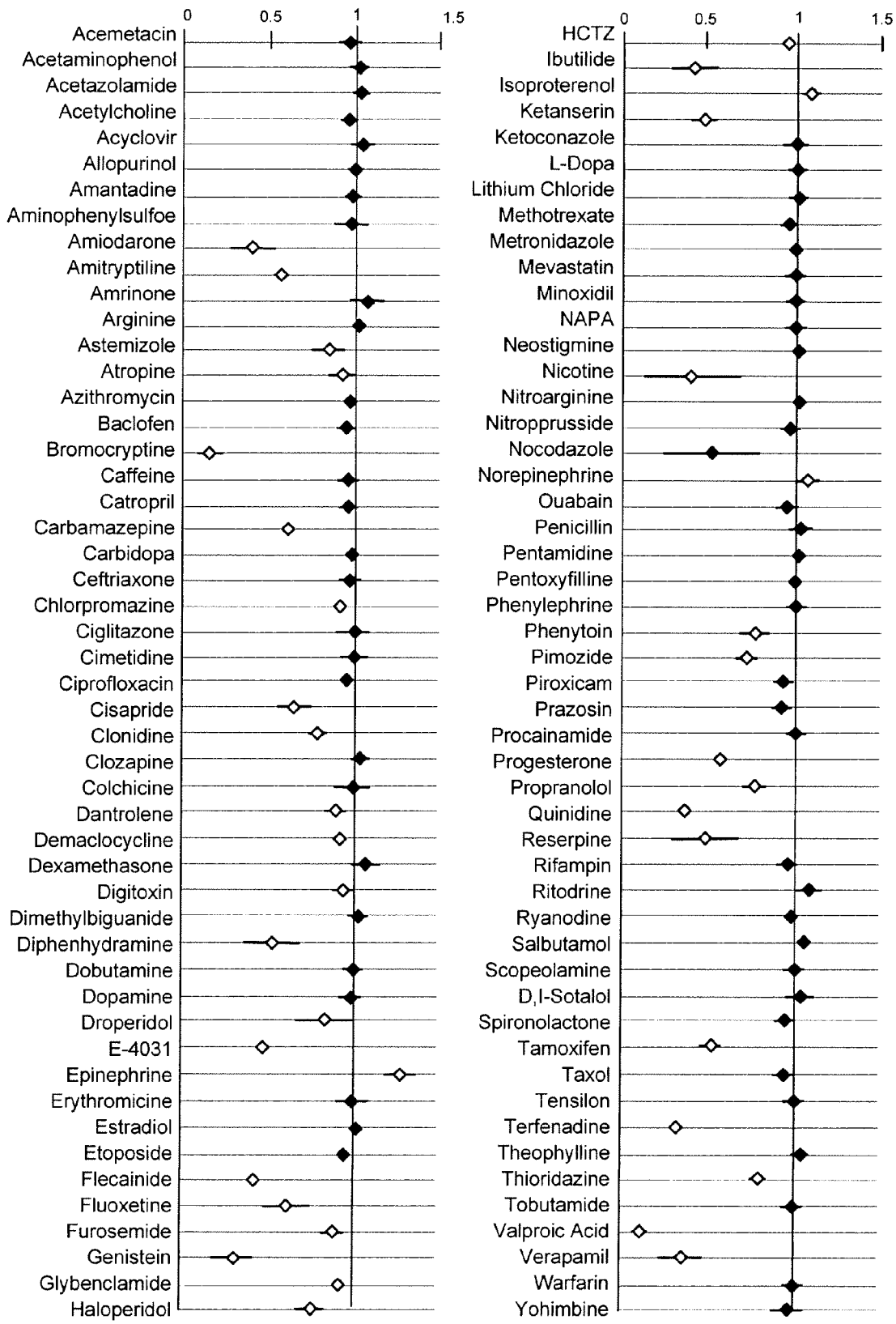
FIG. 1 is a graph showing the results of the initial screen of 100 biologically active small molecules for their effects on the zebrafish HR. HR is plotted as deviation from control (at "1").

FIG. 1 shows the results of the initial screen of 100 biologically active small molecules for their effects on the zebrafish heart rate (HR). Thirty-six compounds resulted in significant bradycardia.

Bradycardia previously has been reported as a result of IKr blockade in several experimental and clinical situations[6, 10]. This effect has been attributed to action potential prolongation[11]. Of the 23 known IKr blockers tested in the initial screen, 18 caused bradycardia in the zebrafish assay. The remaining 5 IKr blocker compounds (erythromycin, N-acetyl-procainamide (NAPA), pentamadine, procainamide, and sotalol) failed to cause bradycardia in the initial zebrafish assay. It was deduced that one, erythromycin, is absorbed from its interaction with cisapride (see FIG. 2C). Poor absorption was determined to be the explanation for the lack of effect of the four other compounds. This explanation is supported by the hydrophilicity of these molecules, each with a logarithm of the octanol:water partition coefficient less than one. Microinjection revealed that these compounds cause bradycardia in the zebrafish once the absorption barrier is bypassed. FIG. 2A demonstrates that bradycardia was seen on direct injection of each drug. Vehicle alone showed no significant effect on HR compared to uninjected zebrafish. Thus, when the microinjection experiments are included, 22 of 23 known IKr blocking agents were positive in this assay.

The hydrophilicity of a drug affects its absorption and may lead to false negatives in an initial screen. However, this problem appears to be predictable from physicochemical characteristics of these molecules, and can be overcome by injection.

This example shows that the methods described herein can, with over 95% reliability, predict or correlate human cardiac response to a compound, e.g., a compound's effects on HR. Potassium depletion of the assay medium can increase sensitivity to QT prolonging drugs.

Calcium-Based Parameters.

The methods described herein can also be used to evaluate a calcium parameter, e.g., in cardiac muscle cells. The animal is modified so that it includes a calcium responsive molecule in heart tissue, e.g., in the cardiac muscle cells. In one embodiment, calcium transients are monitored. For example, it is possible to determine the amount of time required for a calcium transient to be completed. An exemplary parameter is CAT90 which is the time to 90% completion of the calcium transient. Other degrees of completion can also be used. Parameters (such as CAT90) can be normalized, e.g., for heart rate (e.g., using the square root of the preceding RR interval). Other parameters that can be evaluated include calcium transient amplitude, temporal features of the transient other than the CAT 90. Parameters can also be evaluated in a variety of circumstances. For example, it is possible to evaluate calcium responses in the presence of calcium channel inhibitors or agonists and in mutant lines etc., with or without a test compound.

The parameters can be obtained by monitoring a heart, e.g., in the animal (e.g., the zebrafish larva) or removed from the animal. For example, it is possible to take calcium measurements at 3-4 days of development. Heart cells can be monitored, e.g., using microscopy. Embryos can be image on an inverted fluorescence microscope with video capture using a CCD camera. The images can be analyzed using METAMORPH® software. Isochronal maps can be generated.

Using a parameter that is a function of CAT90 normalized by the square root of the preceding RR interval, we found that dofetilide and terfenadine returned parameter values at least 20 or 25% greater than a negative control. Accordingly, drugs that return parameter values greater than about 5, 10, 15, 20, 25, 30, 40% relative to a negative control (such as buffer alone) can be indicated as having an effect on the QT interval.

Calcium Responsive Molecules

A variety of calcium responsive molecules can be used as an indicator to detect changes in calcium. Fluorescent $Ca^{2+}$ indicators such as fura-2, indo-1, fluo-3, and Calcium-Green have been the mainstay of intracellular $Ca^{2+}$ measurement and imaging. See, for example, U.S. Pat. No. 4,603,209 and U.S. Pat. No. 5,049,673. Dyes can be coupled to another moiety, e.g., to dextran.

Dyes can be introduced by a variety of methods. For example, an exemplary method is to inject the dye into an coyote or into an embryo, e.g., at the one cell stage, or at the two or four cell stage. Injection (e.g., at the one cell stage) can be automated) It is also possible to introduce the dye topically, e.g., at stages from 24 hrs post fertilization up to 4/5 days. The dye can be added to the pericardium and then flushed. Injection at one cell stage has not been described and is useful as it can be automated.

It is also possible to use a detectable marker protein that is responsive to calcium. For example, the protein can alter its chemiluminescent or fluorescent properties in response to calcium concentration. One such detectable marker protein is aequorin. Aequorin is available as AQUALITE® from Invitrogen. See also "Imaging [Ca2+]i with aequorin using a photon imaging detector." Miller A L, Karplus E, Jaffe L F. Methods Cell Biol 40, 305-338 (1994) U.S. 20020165364 describes other calcium responsive detectable marker proteins. Such proteins can be introduced by a variety of methods, including microinjection. Typically, such proteins can be produced within one or more cells of a zebrafish, e.g., in a zebrafish embryo, e.g., by expression from a nucleic acid within such cells. For example, the zebrafish can be a transgenic zebrafish that includes a transgene with an expression cassette that contains a sequence encoding the detectable marker protein.

Zebrafish KCNH2 "Knockdown" Experiments

Nearly all of the drugs which have caused clinical QT prolongation in the clinic are known to block a specific current in the cardiac muscle cell named IKr (the rapid component of the cardiac delayed rectifier current). This current is carried by a transmembrane channel formed by at least two gene products, KCNH2 and KCNE2. The products of these genes form a channel through which potassium ions can travel resulting in the IKr current. The cycling cardiac transmembrane electrical potential is a complex phenomenon. Many other membrane channels, additional membrane and cytoskeletal molecules and cellular metabolism are all known to be important determinants of normal and pathological cardiac repolarization.

In order to demonstrate a mechanistic link between IKr blockade and bradycardia in the zebrafish, "knock-down" experiments against the zebrafish ortholog of KCNH2 were performed. An antisense morpholino injected into the embryo elicited bradycardia in a dose-dependent manner. This result, in conjunction with the observed effects of diverse drugs on HR, confirms that IKr blockade results in bradycardia in the zebrafish.

FIG. 2B shows that antisense morpholino oligonucleotides directed against zebrafish KCNH2 demonstrated a dose-dependent effect on HR. Control morpholinos and vehicle alone had no effect on HR.

Not all molecules which result in bradycardia do so through IKr blockade, for example propranolol and clonidine both reduce HR in this assay.

Drug Interactions

Increasing amounts of erythromycin potentiated the effects of cisapride on HR, demonstrating evidence of drug-drug interaction (FIG. 2C). A ten-fold decrease in the ED50 on HR for cisapride is seen with increasing doses of erythromycin. A second example demonstrates the interaction of cimetidine and terfenadine (FIG. 2D).

The recapitulation of these two canonical drug-drug interactions in humans demonstrates a major advantage of this zebrafish model[12]. Both of these interactions have been shown in humans to be pharmacokinetic: the inhibition of hepatic metabolism by one drug resulting in increased levels of the other. Accordingly, this data supports the use of the methods described herein for evaluating pharmacodynamic drug-drug interactions.

The heart rate resolution of the system opens the way for assays not just of cardiotoxicity, but also for any pathway involved in the metabolism of such drugs or other compounds which interact with these drugs, e.g., in the CYP pathways. In one example, one could use molecules that have cardiac effects as reporter molecules to screen for blockers of specific pathways in any biological process.

Pharmacogenomics

Human pharmacogenetic studies of cardiac repolarization have been largely restricted to the evaluation of candidate genes, as more powerful segregation based family studies of drug responses are not feasible[15-18]. The ease of genetic manipulation in the zebrafish allows the identification of inherited modifiers of drug responses.

The assays described herein can be performed with wild-type zebrafish or with zebrafish having one or more genetic alterations. For example, zebrafish having a genetic alteration which diminishes or increases the effect of QT modulating (e.g., QT prolonging) drugs on the heart rate can be screened and identified using the methods described herein. Such mutants allow the identification of inherited modifiers of drug responses, which can be used to identify similar human pharmacogenetic profiles.

In another aspect, such mutants are of use for, e.g., 1) increasing the sensitivity of the assay (e.g., using mutant zebrafish that display increased response to the QT prolonging medications) and 2) increasing the specificity of the assay (e.g., using mutant zebrafish with diminished or no response to QT prolonging medications to prove that a given bradycardic effect is not due to an alternative mechanism).

In addition, differences in the mechanisms of action of IKr blockers may be addressed with this whole animal model. The development of sensitized or resistant zebrafish strains may improve the specificity of this system. The observation that progesterone causes bradycardia, indicates that gender differences in drug-induced repolarization effects may also be accessible[14].

Methods of making transgenic zebrafish are routine in the art and are described, e.g., in Stuart et al. (1988) *Development* 103(2):403-12; Stuart et al. *Development* (1990) 109(3):577-84; Culp et al. (1991) *Proc Natl Acad Sci USA* 88(18):7953-7; U.S. Pat. No. 6,380,458 (making of zebrafish that express transgenes in tissue (e.g., heart)-specific or developmentally (e.g., embryonically)-specific patterns).

Processing Techniques

In any of the methods described herein, a system controller can include hardware, software, or a combination of both to determine and evaluate high-resolution images of the zebrafish, e.g., fluorescent or non-fluorescent zebrafish. Program code is applied to input data to perform the functions described herein and generate output information. The output information is applied to one or more output devices such as a display monitor. For example, the evaluation of a parameter of heart function, e.g., heart rate, can be implemented in computer programs using standard programming techniques. Such programs are designed to execute on programmable computers or dedicated integrated circuits, each comprising a processor, a data storage system (including memory and/or storage elements), at least one input device, and least one output device, such as a display or printer. The program code is applied to input data (e.g., the recorded images from a camera, e.g., a CCD camera) to perform the functions described herein and generate output information (e.g., the high-resolution images), which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis described herein.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, the drawings, and the claims.

EXAMPLES

Example 1

Zebrafish Heart Rate Assay

This example illustrates administration of test agents to zebrafish larvae, and evaluation of heart rate.

Aquaculture

TubingenAB zebrafish embryos were reared in E3 Media (5 mM NaCl, 0.17 mM KCl, 0.33 mM MgCl2, 0.33 mM CaCl2). At 24 hours post fertilization (hpf) the embryos were distributed into 96 well plates, 3-5 embryos per well with 250 ml of E3 supplemented with phenylthiourea at 0.03 g/l to inhibit pigmentation.

Determination of Small Molecule Effects on Heart Rate and Evaluation of Heart Rate Measurement:

At 48 hpf compounds were added to the wells from dimethylsulfoxide (DMSO) stocks so that the final concentration of DMSO remained <2%. DMSO alone was used as a control. HR measurement: 15 second video recordings were obtained from each well using a Nikon TE200 microscope fitted with a computer controlled stage, and a Hamamatsu ORCA-ER camera. One hundred twenty-eight frames with an exposure time of 90 ms were recorded for each video. Digital movies were taken for each well, one from each quadrant. These video clips were stored digitally.

Offline analysis was performed with commercially available imaging software (Metamorph Software, Universal Imaging). The average pixel density was measured for a region of interest over the heart, and these densities were plotted against time. The results were exported in a text file into a standard spreadsheet program (Microsoft Excel). The frequency spectrum was plotted and the peak was reported in a spreadsheet. Manual review of both time domain and frequency domain data as well as the peak frequency was performed to ensure the validity of the data. Fast-Fourier Transform was performed to determine HR. Because some compounds elicited AV block, while others slowed both the atrial and ventricular rates, the ventricular rate was chosen as the most sensitive index of HR effect. Each compound was tested at 1, 10, and 100 mcg/ml and the highest, non-lethal concentration chosen for HR effect. A two-tailed Student's t-test was performed to determine statistical significance.

Microinjections

Micopipettes were pulled on a Sutter JT-8. Zebrafish larvae at 48 hpf were anesthetized using tricaine and 10 mg/ml stock solutions of each compound dissolved in Danieau's solution (58 mM NaCl, 7 mM KCl, 0.4 mM MgSO4, 6 mM Ca(NO3)2, 5.0 mM HEPES pH 7.6) were injected into the yolk sac. Pressure was adjusted to deliver approximately 5 nL. The fish were allowed to recover for 4 hours before recording HR.

Approximately 5 nL of the morpholino antisense oligonucleotide diluted in Danieau's solution at the concentrations shown were injected into the zebrafish embryo at the single cell stage[9]. The zebrafish KCNH2 morpholino was directed against the splice donor site of the sixth exon of the zebrafish KCNH2 ortholog (5'-CCGTCGTACAGGCATGTTGTC-CTA-3'; SEQ ID NO:2).

Results are shown in FIGS. 1 and 2.

Example 2

Transgenic Zebrafish

This example illustrates the making of a transgenic zebrafish that can be used in the methods described herein.

A 5.1 Kb fragment of the cardiac myosin light chain (cmlc) regulatory region was used to drive expression of GFP specifically to myocardial cells in both cardiac chambers of the zebrafish. Expression is mosaic in the heart in founders and uniform after germ-line transmission. These zebrafish can be used in the methods described herein to evaluate parameters of heart function though detection of the fluorescent larval heart.

The minimal promoter sequence of the zebrafish cmlc gene was identified by conventional techniques. A 150 base pair fragment of the promoter region (SEQ ID NO:1) is necessary and sufficient for driving embryonic cardiac expression:

```
GTCCCCCTCCCCATCTGCACACTTTATCTCATTTTCC  (SEQ ID NO:1)
ACCCTGCTGGAATCTGAGCACTTGTGCAGTTATCAGG
GCTCCTGTATTTAGGAGGCTCTGGGTGTCCATGTAGG
GGACGAACAGAAACACTGCAGACCTTTATAGAAGAAC
AA
```

This fragment can be used to drive expression of GFP specifically to myocardial cells in both cardiac chambers of the zebrafish as well.

Example 3

High Throughout Assay Using Transgenic Zebrafish

This example illustrates the performance of the methods described herein in a high-throughput format, using zebrafish having fluorescent heart tissue.

General Principle:

Transgenic zebrafish embryos that express GFP in the heart, as described herein, are arrayed into 96-well plates at 3+ embryos per well. The plate is systematically scanned with a NIKON TE 200 microscope equipped with an automated stage and controlled by Metamorph® software (Universal Imaging Corporation). Metamorph journals (macros) allow for automatically scanning the entire plate, identifying and imaging each fluorescent heart, and using measurements from the images to calculate individual heart rates. The heart rates are outputted in such a way that allows for the rapid identification of wells that contain embryos with rates that are abnormally high or low. This system quickly identifies chemicals and/or genetic mutations that increase or decrease embryonic heart rates. The system can be configured to monitor calcium responsive molecules, e.g., to provide information about calcium transients or other calcium-based parameters at the different positions on the plate.

MLC2a::mGFP5 Transgenic Zebrafish:

Standard methods (Gilmour et al. (2002). *Manipulating Gene Expression in Zebrafish*. In *Zebrafish*, C. Nusslein-Volhard and R. Dahm, eds. (Oxford, UK: Oxford University Press)) were used to create zebrafish that express green fluorescent protein (GFP) uniformly in embryonic atrial and ventricular cardiomyocytes beginning at 24 hours post-fertilization and beyond day 5.

The zebrafish myosin light chain 2a promotor is used to drive expression of GFP. Although transient expression of proteins following injection of DNA is mosaic, uniform expression can be achieved by generating stable transgenic zebrafish that contain the transgene integrated into the zebrafish genome (Gilmour et al., supra). Stable transgenic zebrafish are generated by injecting one-cell stage embryos with the transgene, raising the injected embryos to sexual maturity, and then screening their offspring for uniform expression of the protein. Positive offspring are heterozygous for the transgene. Using these methods, stable transgenic zebrafish line (MLC2a::GFP) was generated that expresses GFP specifically and uniformly in all atrial and ventricular cardiomyocytes. Like transient expression, stable expression begins at approximately 24 hours and persists through day 5 and into adulthood. Heterozygous transgenic zebrafish were intercrossed to generate homozygous transgenic zebrafish. There is no overt toxicity seen in either the heterozygous or homozygous embryos or adult zebrafish. It is believed that this is the first transgenic zebrafish made that expresses any protein (fluorescent or non-fluorescent) specifically in the embryonic heart. The MLC2a::GFP transgenic line can be used in the methods described herein. It can also be useful for isolating intact embryonic hearts and embryonic cardiomyocytes from dissociated embryos.

The fish are imaged at day 3 post-fertilization. At this time, the embryos are out of their chorions and rest on the bottoms of the wells. For this assay, the orientation of the embryos does not matter.

Scanning the Plate and Identifying Fluorescent Hearts:

Through the use of journals (macros), an algorithm was developed in the METAMORPH® software for systematically scanning a 96-well plate and identifying fluorescently-tagged hearts. The algorithm performs the following functions: Each well is visited by the microscope's objective. Within each well, 4 adjacent but non-overlapping quadrants are considered separately. Each quadrant is imaged under fluorescent light and the maximum intensity in the image is calculated. If one or more fluorescent hearts are present in the quadrant, then the maximum intensity in the image will fall above a threshold that was determined empirically. If no fluorescent hearts are present, then the maximum intensity in the image will fall below the threshold. Using a branching variable, the microscope will either move to the next quadrant if no hearts are detected or launch a series of operations if a heart is present in the quadrant. It is also possible to image the entire wells without breaking them down into quadrants. It is also possible to divide each well into up to 16 subsections and each could be analyzed individually. For analyzing heart rates, using 4 subsections is preferred.

Imaging the Fluorescent Hearts and Analyzing the Images:

When a heart is identified in a quadrant, the microscope and software together perform a series of operations controlled by the Metamorph journals. The microscope's objective autofocuses on the heart and takes a short video of it beating. The video is then processed in the following manner. A "region" that is fixed in size is created around the heart in the first frame of the video. For each subsequent frame of the video, the average intensity within that same fixed region is calculated. As the heart beats, the average intensity will vary based on the movement of the heart and, when plotted through time, the average intensity reflects the heart's periodicity. For each heart within a video, the average intensity through time data are calculated and deposited into a log file. Each heart is analyzed separately and up to 12 hearts per video have been imaged and analyzed successfully. Videos of variable lengths (either 32, 64, 128, or 256 frames at a rate of approximately 18 frames per second) can be used. The larger numbers of frames yield more accurate heart rates but take longer to acquire.

Analysis of the Log File:

Throughout the course of the plate being scanned, a sizeable dataset or "log file" is generated. The log file contains a record of all of the individual operations of the microscope during the run. For instance, every time a quadrant is visited and analyzed for maximum intensity, a text message about that operation is deposited in the log file regardless of whether a heart is present in the quadrant. In addition, as described above, every time a heart is analyzed, the average intensity through time data are also deposited in the log file. Therefore, the log file contains relevant data (the average intensity through time for each heart) embedded within extraneous information about the run. A Visual Basic program can be readily developed to (a) scan the log file and (b) extract the average intensity through time data for each heart and (c) disregard or discard extraneous information. The average intensity through time data are processed with a Fast Fourier Transform function and heart rates are determined. Individual heart rates and averages for each well are outputted to a MS excel spreadsheet in a format that allows one to rapidly identify wells that contain embryos with abnormally high or low heart rates.

Example 4

Isolation of Embryonic Hearts and Cardiomyocytes

This example describes the isolation of hearts and cardiomyocytes from MLC2a::GFP transgenic zebrafish embryos described herein.

As described herein, it has been demonstrated that zebrafish embryos can be used to identify agents that are potentially cardiotoxic in humans. It was shown that 22 of 23 agents that cause repolarization abnormalities in humans caused similar effects in the zebrafish cardiotoxicity assay. Eighteen of the 23 agents caused cardiotoxicity following addition of the agent to the embryonic medium. Four of the agents, however, were not absorbed efficiently into the embryo as an effect was seen only following injection of these agents into the embryo.

To circumvent the absorption barrier and increase the sensitivity of the assay one can study the effects of agents on purified hearts or cardiomyocytes. The MLC2a::GFP transgenic line makes purification of hearts and cardiomyocytes possible. Embryos are dissociated by treatment with a mucolytic agent (e.g. Dithiothreitol, N-acetyl cysteine, cysteine, and/or other mucolytic agent) and protease (e.g. collagenase) or by mechanical dissociation (e.g. passage through a needle, e.g., a 19G needle, or similar method) and the embryonic hearts are released intact from the embryo. The hearts can be identified under fluorescent light by virtue of GFP expression and collected manually. Alternatively, released hearts can be enzymatically digested to completion and individual GFP+ cardiomyocytes purified from other embryonic cells by fluorescence activated cell sorting. Purified hearts and cardiomyocytes can be used in a host of biological and electrical assays, including assays to identify agents that cause cardiotoxicity.

Example 5

Permeabilization of Zebrafish

Once can also circumvent the absorption barrier and increase the sensitivity of the assay by permeabilizing the fish, e.g., by using high throughput enzymatic digestion. The following exemplary protocol for permeabilization can be used.

1. Wash 3-day old larvae with either Cell dissociation buffer (CBD, Gibco/BRL) or Ca-free HBSS (10×Ca-free HBSS: NaCl 80 g/L, KCl 4 g/L, $MgCl_2.6H_2O$ 1 g/L, $MgSO_4.7H_2O$ 1 g/L, $Na_2HPO_4$ 0.48 g/L, $KH_2PO_4$ 0.6 g/L, $NaHCO_3$ 3.5 g/L, Glucose 10 g/L) at least twice with complete exchanges in a Eppendorf tube. For the CBD this is best done at room temperature.

2. To the washed embryos add 1 ml of proteinase K (80 ug/ml in CDB) and gently invert the Eppendorf for 2 minutes.

3. Immediately remove all the proteinase K solution, and exchange in $Ca^{2+}$ HBSS ($Ca^{2+}$ HBSS: 800 uL of 1M $CaCl_2$ to each liter of 1×Ca free HBSS).

4 Completely exchange the $Ca^{2+}$ HBSS at least 4 times.

Example 6

Cardiac-specific Co-expression Methods

This example describes the construction of a vector for identifying, monitoring, and/or evaluating cardiomyocytes that overexpress any protein of interest.

It is possible to transiently overexpress proteins for several days in the zebrafish embryonic heart by injecting a transgene containing the MLC2a promoter upstream of a cDNA of interest. The distribution of the injected DNA is mosaic and therefore, only a fraction of the cardiomyocytes will overexpress the protein of interest. Unless the expressed protein is detectable, it is impossible to identify the expressing cardiomyocytes in live embryos. To circumvent this difficulty, the invention features cardiac co-expression constructs that can simultaneously direct expression of any protein of interest and a detectable, e.g., fluorescent, marker (such as GFP, nuclear-dsRed2 or membrane-YFP) in embryonic cardiomyocytes. The fluorescent protein serves as a marker for the cardiomyocytes expressing the protein of interest.

The cardiac co-expression plasmids contains two expression cassettes in a single DNA construct. Both expression cassettes contain the cardiac-specific MLC2a promoter. In the first cassette, the promoter drives expression of a fluorescent protein (GFP, nuclear-dsRed2, or membrane YFP or other fluorescent protein) in embryonic in cardiomyocytes. The second expression cassette contains the MLC2a promoter, a multi-cloning site (MCS) and a polyadenylation signal. The cDNA for any protein of interest can be cloned into the multi-cloning site and it will be co-expressed with the fluorescent protein in embryonic cardiomyocytes (or other suitable detectable marker).

As a proof or principle, the GFP cDNA was cloned into the MCS of a nuclear ds-Red2 co-expression plasmid, the resulting construct was injected into early zebrafish embryos, and the embryos were analyzed for expression of cardiac-nuclear-dsRed2 and cardiac-GFP at 50 hours post fertilization. Nuclear-dsRed2 and GFP were both visible in a fraction of the cardiomyocytes and there mosaic expression patterns perfectly overlapped. Thus, any cardiomyocyte that expressed nuclear-dsRed2 also expressed GFP. Therefore, it is possible to use nuclear-dsRed2 (or another fluorescent protein) as a marker for cardiomyocytes that express any protein of interest. This strategy can be utilized to overexpress two or more proteins in zebrafish cardiomyocytes and evaluate the effects of overexpression on any aspect of cardiomyocyte biology. A similar strategy has been previously used to demonstrate that over-expression of Reptin enhances embryonic cardiomyocyte proliferation (Rottbauer et al., 2002). However, since the expression cassettes used by Rottbauer et al. were carried on two different plasmids, co-segregation could not be guaranteed. By placing the expression cassettes into one DNA construct, co-segregation and co-expression is assured.

These co-expression constructs can be used to implicate candidate proteins in QT prolongation, for structure/function studies on proteins known to cause QT prolongation, and for assaying how overexpression of any protein modifies the heart's and/or cardiomyocyte's response to treatment with chemical agents.

Example 7

Figure 3A:
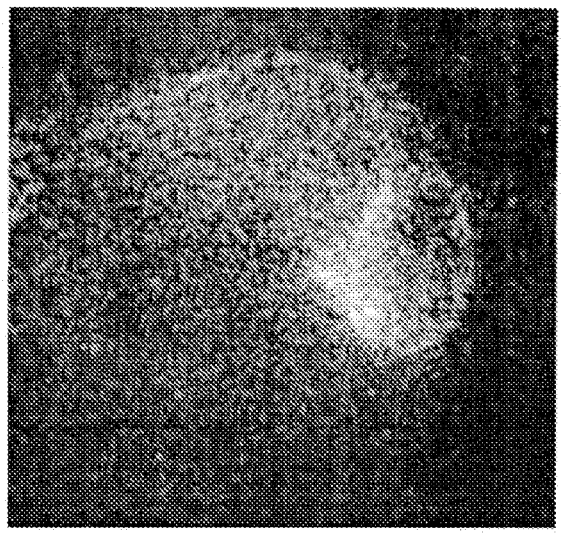
FIG. 3A is an image of a calcium responsive dye in a zebrafish embryo.
Figure 3B:
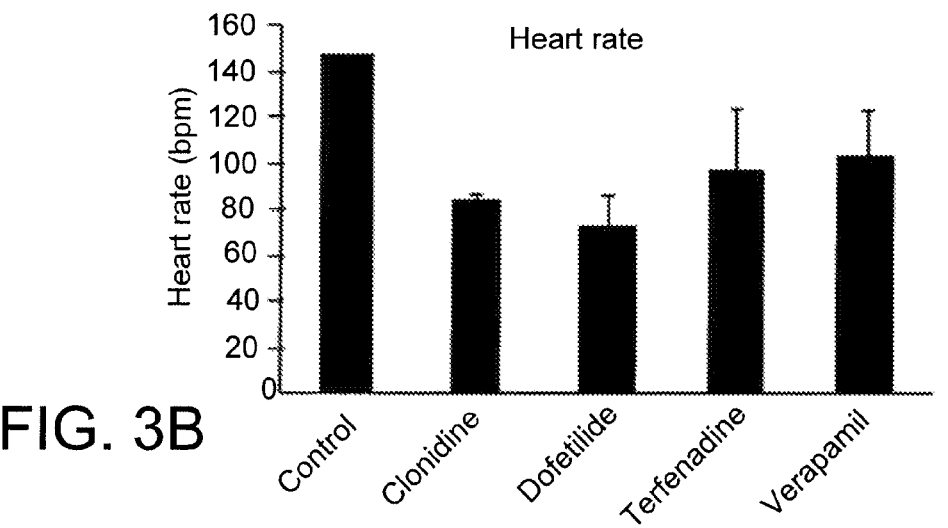
FIG. 3B is a graph of heart rate in the presence of different compounds.
Figure 3C:
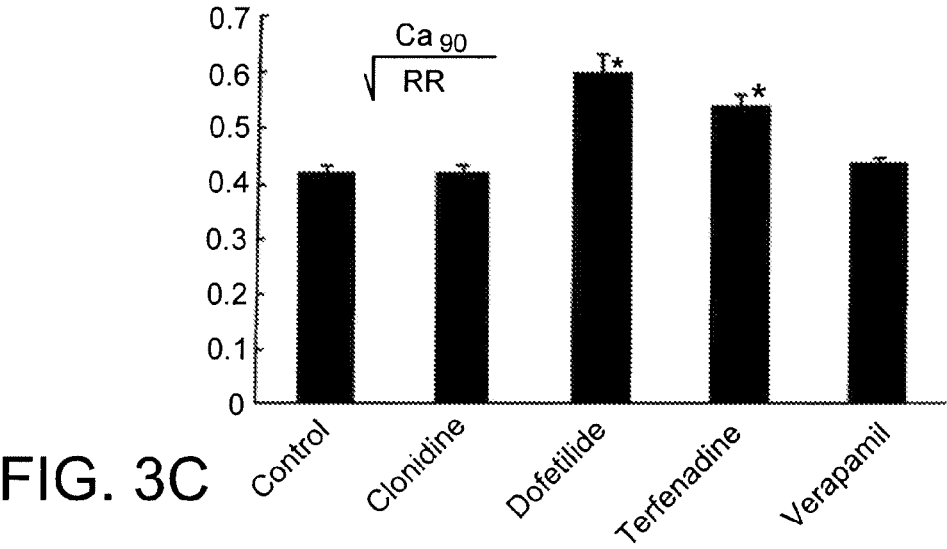
FIG. 3C is a graph of a CAT90-based parameter in the presence of different compounds.

Embryos at the single cell stage were injected (into the cell body of the cell) with dextran-coupled calcium-green (Molecular Probes, Eugene Oreg.) of an average MW of 3,000 g/mol. Embryos were then allowed to develop in a dark environment before imaging at the indicated time on an inverted fluorescence microscope with video capture using a CCD camera. The images were analyzed off-line with META-MORPH® software and isochronal maps were generated. In addition, using a single reference point in the ventricle, CAT90 (the time to 90% completion of the calcium transient) was determined. These data were then corrected for the heart rate (using the square root of the preceding RR interval) and plotted as shown in FIG. 3C. It was possible to discriminate IKr blockers from other mechanisms of bradycardia using appropriate cutoffs of CAT90 despite a range of effects on heart rate.

All cited publications and patents are hereby incorporated by reference in their entirety. A number of embodiments of the invention have been described. Nevertheless, it will be understood that various modifications may be made without departing from the spirit and scope of the invention. Accordingly, other embodiments are within the scope of the following claims.

REFERENCES

1. Camm, A. J., M. J. Janse, D. M. Roden, et al. Congenital and acquired long QT syndrome. Eur Heart J, 2000. 21(15): 1232-7.
2. Keating, M. T. and M. C. Sanguinetti. Molecular and cellular mechanisms of cardiac arrhythmias. Cell, 2001. 104 (4): 569-80.
3. Roden, D. M. Pharmacogenetics and drug-induced arrhythmias. Cardiovasc Res, 2001. 50(2): 224-31.
4. Antzelevitch, C. and J. Fish. Electrical heterogeneity within the ventricular wall. Basic Res Cardiol, 2001. 96(6): 517-27.
5. Yang, T., D. Snyders, and D. M. Roden. Drug block of I(kr): model systems and relevance to human arrhythmias. J Cardiovasc Pharmacol, 2001. 38(5): 737-44.
6. Eckardt, L., W. Haverkamp, M. Borggrefe, et al. Experimental models of torsade de pointes. Cardiovasc Res, 1998. 39(1): 178-93.
7. Baker, K., K. S. Warren, G Yellen, et al. Defective "pacemaker" current (Ih) in a zebrafish mutant with a slow heart rate. Proc Natl Acad Sci U S A, 1997. 94(9): 4554-9.
8. Warren, K. S. and M. C. Fishman. "Physiological genomics": mutant screens in zebrafish. Am J Physiol, 1998. 275(1 Pt 2): H1-7.
9. Nasevicius, A. and S. C. Ekker. Effective targeted gene 'knockdown' in zebrafish. Nat Genet, 2000. 26(2): 216-20.
10. De Clerck, F., A. Van de Water, J. D'Aubioul, et al. In vivo measurement of QT prolongation, dispersion and arrhythmogenesis: application to the preclinical cardiovascular safety pharmacology of a new chemical entity. Fundamental & Clinical Pharmacology, 2002. 16: 125-140.
11. Verheijck, E. E., A. C. van Ginneken, J. Bourier, et al. Effects of delayed rectifier current blockade by E-4031 on impulse generation in single sinoatrial nodal myocytes of the rabbit. Circ Res, 1995. 76(4): 607-15.
12. Roden, D. M. Acquired long QT syndromes and the risk of proarrhythmia. J Cardiovasc Electrophysiol, 2000. 11(8): 938-40.
13. Antzelevitch, C., Z. Q. Sun, Z. Q. Zhang, et al. Cellular and ionic mechanisms underlying erythromycin-induced long QT intervals and torsade de pointes. J Am Coll Cardiol, 1996. 28(7): 1836-48.
14. Pharm, T. V. and M. R. Rosen. Sex, hormones, and repolarization. Cardiovasc Res, 2002. 53(3): 740-51.
15. Yang, P., H. Kanki, B. Drolet, et al. Allelic variants in long-QT disease genes in patients with drug-associated torsades de pointes. Circulation, 2002. 105(16): 1943-8.

16. Sesti, F., G. W. Abbott, J. Wei, et al. A common polymorphism associated with antibiotic-induced cardiac arrhythmia. Proc Natl Acad Sci U S A, 2000. 97(19): 10613-8.
17. Roden, D. M. and A. L. George, Jr. The genetic basis of variability in drug responses. Nat Rev Drug Discov, 2002. 1(1): 37-44.
18. Splawski, I., K. W. Timothy, M. Tateyama, et al. Variant of SCN5A sodium channel implicated in risk of cardiac arrhythmia. Science, 2002. 297(5585): 1333-6.
19. Rottbauer et al. (2001) Developmental Cell, Vol 1, 265-275
20. Barrionuevo and Burgren; Am J Physiol 1999 February; 276(2 Pt 2):R505-13
21. Warren et al.; Am J Physiol Heart Circ Physiol 2001 October;281(4):H1711-9

What is claimed is:

1. A method of evaluating a test agent for the ability to modulate a parameter of heart function in a mammal, the method comprising:
   (a) introducing a calcium-responsive molecule to a zebrafish heart, wherein the calcium-responsive molecule is not expressed from a transgene;
   (b) contacting the zebrafish heart with a test agent; and
   (c) evaluating a calcium-based parameter of heart function in the zebrafish heart, wherein modulation of the parameter compared to the parameter evaluated in the absence of the test agent is an indication that the test agent has the ability to modulate a parameter of heart function in a mammal.

2. The method of claim 1, further comprising: (d) correlating the effect of the agent on the parameter of heart function in the zebrafish with a predicted effect on heart function in a mammal.

3. A method of evaluating a test agent for the ability to modulate a parameter of heart function in a mammal, the method comprising:
   (a) introducing a calcium-responsive molecule to a zebrafish heart, wherein the calcium-responsive molecule is not expressed from a transgene;
   (b) contacting the zebrafish heart with a test agent; and
   (c) evaluating a parameter of heart function in the zebrafish heart, wherein the parameter is an assessment of a calcium transient, wherein modulation of the parameter compared to the parameter evaluated in the absence of the test agent is an indication that the test agent has the ability to modulate a parameter of heart function in a mammal.

4. The method of claim 3, wherein the parameter is an assessment of the time for 90% completion of the calcium transient.

5. The method of claim 3, wherein the parameter is an assessment of calcium transient amplitude.

6. The method of claim 1, wherein the zebrafish is a wild-type zebrafish larva.

7. The method of claim 1, wherein the zebrafish is a zebrafish larva.

8. The method of claim 1, further comprising contacting the zebrafish heart with a second test agent.

9. The method of claim 1, wherein the method is performed in an array format.

10. A method of evaluating a test agent for the ability to modulate a parameter of heart function in a mammal, the method comprising:
    (a) contacting a zebrafish heart with a test agent, wherein the heart includes cells that comprise a calcium-responsive molecule, wherein the calcium responsive molecule is a detectable marker protein or a dye, and wherein the calcium-responsive molecule is not expressed from a transgene; and
    (b) evaluating a calcium-based parameter of heart function in the zebrafish heart, wherein modulation of the parameter compared to the parameter evaluated in the absence of the test agent is an indication that the test agent has the ability to modulate a parameter of heart function in a mammal.

11. The method of claim 1, further comprising permeabilizing the zebrafish prior to or concurrently with step (a), step (b), or step (c).

12. The method of claim 1, wherein the test agent is evaluated in combination with a second test agent.

13. The method of claim 1, wherein the test agent is a small molecule.

14. The method of claim 1, wherein the test agent is a protein.

15. The method of claim 1, wherein the heart is evaluated within an intact zebrafish.

16. The method of claim 1, wherein a plurality of compounds is evaluated, at least some of which are evaluated in parallel.

17. The method of claim 1, wherein the calcium responsive molecule is administered to a zebrafish larva prior to or concurrently with the step of contacting.

18. The method of claim 17, wherein the calcium responsive molecule is administered topically.

19. The method of claim 17, wherein the calcium responsive molecule is administered by injection.

20. The method of claim 1, wherein the calcium responsive molecule is injected aequorin.

21. The method of claim 10, wherein the detectable marker protein is aequorin.

22. The method of claim 1, further comprising:
evaluating a parameter of heart function selected from heart rate, blood flow, contraction fraction, ejection fraction, repolarization, calcium flux, calcium concentration, conduction velocity, presence of an atrioventricular (AV) block, and QT interval, in the zebrafish heart.

23. The method of claim 10, further comprising:
evaluating a parameter of heart function selected from heart rate, blood flow, contraction fraction, ejection fraction, repolarization, calcium flux, calcium concentration, conduction velocity, presence of an atrioventricular (AV) block, and QT interval, in the zebrafish heart.

24. The method of claim 1, further comprising:
introducing a voltage-sensitive dye to the zebrafish heart; and
visualizing the voltage-sensitive dye.

25. The method of claim 10, further comprising:
contacting the zebrafish heart with a voltage-sensitive dye; and
visualizing the voltage-sensitive dye.

26. The method of claim 1, wherein the calcium-responsive molecule is selected from the group consisting of calcium green, fura-2, indo-1, and fluo-3.

27. The method of claim 10, wherein the calcium-responsive dye is selected from the group consisting of calcium green, fura-2, indo-1, and fluo-3.

* * * * *

SEQUENCE LISTING

<160> NUMBER OF SEQ ID NOS: 2

<210> SEQ ID NO 1
<211> LENGTH: 150
<212> TYPE: DNA
<213> ORGANISM: Danio rerio

<400> SEQUENCE: 1
gtccccctcc ccatctgcac actttatctc attttccacc ctgctggaat ctgagcactt    60
gtgcagttat cagggctcct gtatttagga ggctctgggt gtccatgtag gggacgaaca   120
gaaacactgc agacctttat agaagaacaa                                    150

<210> SEQ ID NO 2
<211> LENGTH: 24
<212> TYPE: DNA
<213> ORGANISM: Danio rerio

<400> SEQUENCE: 2
ccgtcgtaca ggcatgttgt ccta                                           24